United States Patent [19]
de Soyres et al.

[11] 4,371,471
[45] Feb. 1, 1983

[54] HYDROCARBON STOCK SOLUTIONS OF $CR^{+6}$ COMPOUNDS STORAGE-STABILIZED BY A SOLUBLE PARTIAL ESTER OF A PHOSPHORIC ACID

[75] Inventors: Bruno de Soyres, Mulhouse; Jacques Nouvel, Tassin la Demi-Lune, both of France

[73] Assignee: Rhone-Poulenc Industries, Paris, France

[21] Appl. No.: 171,088

[22] Filed: Jul. 22, 1980

[30] Foreign Application Priority Data

Jul. 26, 1979 [FR] France ............................... 79 19738

[51] Int. Cl.$^3$ ..................... C07F 11/00; B01J 31/12
[52] U.S. Cl. ..................... 260/438.5 R; 252/431 P
[58] Field of Search ........................... 260/438.5

[56] References Cited

U.S. PATENT DOCUMENTS

| | | | |
|---|---|---|---|
| 2,777,874 | 1/1957 | Asseff et al. | 260/438.5 |
| 3,346,492 | 10/1967 | Hess | 260/438.5 |
| 3,474,080 | 10/1969 | Rekers | 260/438.5 |
| 3,477,953 | 11/1969 | Carlson | 260/438.5 |
| 3,907,849 | 9/1975 | Meyer | 260/438.5 R |

*Primary Examiner*—Charles F. Warren
*Assistant Examiner*—Raymond Covington
*Attorney, Agent, or Firm*—Burns, Doane, Swecker & Mathis

[57] ABSTRACT

Hydrocarbon solvent solutions of hexavalent chromium compounds are storage-stabilized by incorporating therein precipitation stabilizing amounts of a soluble partial ester of a phosphoric acid; such are useful catalyst stock solutions.

16 Claims, No Drawings

HYDROCARBON STOCK SOLUTIONS OF CR+6 COMPOUNDS STORAGE-STABILIZED BY A SOLUBLE PARTIAL ESTER OF A PHOSPHORIC ACID

BACKGROUND OF THE INVENTION

1. Field of the Invention

The present invention relates to the stabilization of solutions of organic compounds of hexavalent chromium in hydrocarbon solvents, and, more especially, to the stabilization of such solutions utilizing stabilizing amounts of partial esters of phosphoric acid.

2. Description of the Prior Art

It is known to this art that organic chromium compounds, and in particular its carboxylic acid salts, its chelates with dicarbonyl compounds or the chromates of tertiary alcohols, are well adapted for the catalysis of various reactions, such as the dimerization of diolefin compounds, the oxidation of cycloaliphatic or alkylaromatic hydrocarbons with air, the hydrogenation of olefinic double bonds in hydrocarbon polymers, the decomposition of organic hydroperoxides, or the crosslinking of polymers comprising carboxyl functions by means of epoxy compounds. And the chromates of tertiary alcohols remain useful as oxidizing agents.

To carry out the aforesaid various reactions, it is often times advantageous to use the chromium derivatives in the form of a solution in a hydrocarbon solvent, such as an alkane, cycloalkane or aromatic hydrocarbon solvent. In the case of reactions carried out continuously, it is typically convenient to have a supply of catalyst solution readily available. However, it has been found that these solutions are not stable with passage of time and ultimately result in the precipitation of the metal as chromium oxide. A phenomenon of such type is especially deleterious because it causes both blocking of the pumps and feed pipes and variations in the concentrations of the catalyst solutions, and this jeopardizes the steady progress of the reactions in question.

This precipitation phenomenon is the more marked, the longer the solutions are stored.

SUMMARY OF THE INVENTION

Accordingly, a major object of the present invention is the provision of improved, storage-stable solutions of hexavalent chromium catalysts in hydrocarbon solvents, which solutions can be stored over prolonged periods of time without the chromium being precipitated therefrom.

Briefly, the present invention features the stabilization of solutions of hexavalent chromium compounds in hydrocarbon solvents, characterized by incorporating into such solutions a stabilizing amount of a phosphoric acid ester which contains at least one free acid group and which is soluble in the particular hydrocarbon solvent selected.

DETAILED DESCRIPTION OF THE INVENTION

More particularly according to this invention, preferred stabilizers are the orthophosphoric acid esters or the polyphosphoric acid esters, or also any admixture of such esters. Phosphoric or polyphosphoric acid esters are compounds per se known to the literature; compare, for example, the treatise of Houben-Weyl, *Methoden der organischen Chemie* (Methods of Organic Chemistry), Volume XII/2; *Organische Phosphorverbindungen* (Organic Phosphorus Compounds) (1964).

Among the orthophosphoric acid esters which are useful herein, representative are those of the structural formula:

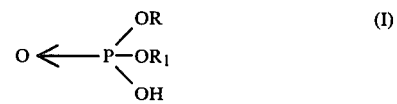

in which R represents a saturated hydrocarbon radical containing from 1 to 18 carbon atoms and $R_1$ represents a hydrogen atom or one of the radicals represented by R. The radicals R and $R_1$ can be identical or different. Among the esters of the formula (I), those in which at least one of the radicals R or $R_1$ contains more than 3 carbon atoms are preferred.

The symbol R can represent, for example, a linear or branched chain alkyl radical, such as a methyl, ethyl, isopropyl, butyl, t-butyl, heptyl, octyl, dodecyl or octadecyl radical, a cycloalkyl radical, such as a cyclohexyl, cyclooctyl, cyclododecyl or menthyl radical, an aryl radical, such as a phenyl or tolyl radical, or an aralkyl radical, such as a benzyl or phenylethyl radical.

The orthophosphoric acid esters intended include, in particular, methyl n-butyl orthophosphate, ethyl octyl orthophosphate, monobutyl orthophosphate, dibutyl orthophosphate, diisobutyl orthophosphate, monoheptyl orthophosphate, diheptyl orthophosphate, mono-(2-ethylhexyl) orthophosphate, di-(2-ethylhexyl) orthophosphate, monodecyl orthophosphate, didodecyl orthophosphate, monooctadecyl orthophosphate, dioctadecyl orthophosphate, methyl cyclohexyl orthophosphate, monocyclohexyl orthophosphate, dicyclohexyl orthophosphate, monobenzyl orthophosphate, methyl benzyl orthophosphate, ethyl tolyl orthophosphate, monomethyl orthophosphate and n-dodecyl cyclohexyl orthophosphate.

In the phosphates of the formula (I), the precise nature of the radical R is not critical in terms of attaining the desirable result consistent herewith; rather, the same is selected only to ensure the solubility of the phosphate in the hydrocarbon solvent. R is preferably a branched chain alkyl radical.

Among the polyphosphoric acid esters intended, the pyrophosphoric acid esters, tripolyphosphate esters, and the like, are representative. The pyrophosphoric acid esters are notably advantageous, the same being represented by the following structural formula:

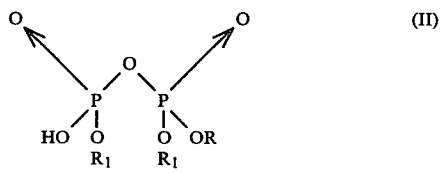

wherein the various symbols $R_1$ and R are as above defined. By way of illustration, the following acid pyrophosphate esters are exemplary: dimethyl pyrophosphate, diethyl pyrophosphate, dibutyl pyrophosphate, diisobutyl pyrophosphate, dioctyl pyrophosphate, di-(2-ethylhexyl) pyrophosphate, butyl benzyl pyrophosphate and the like.

To carry out the process according to the invention, it is optional to use but a single such phosphoric acid ester, or any mixture of any two or more than two such phosphoric acid esters. The nature of the various esters is not critical; as already mentioned, same must simply ensure the solubility of the phosphates in the hydrocarbon solvents. The mixture can be based on orthophosphates or pyrophosphates, or it can also include at least one orthophosphate and at least one pyrophosphate. Depending on the nature of the solution of the organic chromium compound, it can be advantageous to use a mixture of esters consisting of one orthophosphate and one pyrophosphate. As a general rule, and in the case of solutions of tertiary alkyl chromates, a mixture of this type advantageously contains from 5 to 30% by weight of the "pyro" derivative.

These mixtures can be synthetic, or formulated mixtures, or same can be directly obtained, for example, by reacting alkanols with $P_2O_5$ or with a mixture of orthophosphoric acid and polyphosphoric acid.

The mixtures of phosphoric acid esters contain free acid groups and can consist of esters which contain, relative to the phosphorus atom, an identical or different number of free acid groups. This formulation is desirable in that it is thus possible to readily determine and select that proportion of free acid groups which results in the best stability and the best solubility. In this context, mixtures containing from 50 to 90% of a dialkyl orthophosphate are well suited for purposes of this invention, with the remainder consisting, for example, of a dialkyl pyrophosphate or a monoalkyl orthophosphate.

It has also been determined that a mixture of the immediately aforesaid type is particularly well adapted for stabilizing solutions of tertiary alkyl chromates in hydrocarbon solvents.

The nature of the hexavalent chromium compounds which are dissolved in the hydrocarbon solvents and which are stabilized by the phosphoric acid partial esters consistent with the invention can widely vary. In general, such compounds are obtained from chromium trioxide, $CrO_3$, and their chemical constitution corresponds more particularly to that of the anions $[Cr_nO_{3n+1}]^{2-}$, n being an integer equal to 1, 2, 3 or 4. These compounds are per se described, for example, in: *Gmelin Handbuch der anorganischen Chemie* (Gmelin's Handbook of Inorganic Chemistry), *Chrom* (Chromium), Part C (1965), and Pascal, *Traité de Chimie minérale* (Treatise of Inorganic Chemistry), Volume XIV.

The process according to the invention is especially adopted for the stabilization of chromates of aliphatic and cycloaliphatic tertiary alcohols containing from 4 to 20 carbon atoms, such as tert.-butyl alcohol, t-amyl alcohol, 2-methylpentan-3-ol, 2-methylhexan-2-ol, dimethylpentadecylcarbinol, 2-methylcyclohexanol and 1-ethylcyclohexanol. These compounds are obtained by reacting chromium trioxide with tertiary alcohols in accordance with the techniques described, for example, in U.S. Pat. No. 3,287,082, and in the *Journal of the American Chemical Society*, 78, 1,694–8 (1955).

Particular examples which may be mentioned of chromates of tertiary alcohols are t-butyl chromate, t-amyl chromate, dimethylpentadecylcarbinol chromate and 1-methylcyclohexyl chromate.

Exemplary of the hydrocarbon solvents in which solutions of chromium derivatives can be stabilized by the addition of soluble acid phosphates thereto are linear or branched chain alkanes containing from 5 to 20 carbon atoms, such as n-pentane, n-hexane, 2-methylpentane, 3-methylpentane, 2,3-dimethylbutane, n-heptane and n-pentadecane, cycloalkanes containing from 5 to 9 carbon atoms and optionally containing from 1 to 3 alkyl substituents having from 1 to 4 carbon atoms, such as cyclopentane, cyclohexane, cycloheptane, cyclooctane and methylcyclohexane, and aromatic hydrocarbons, such as benzene, toluene, xylenes and ethylbenzene. The process according to the invention is very particularly applicable to the stabilization of solutions of chromium (VI) compounds in cycloalkanes.

The concentration in the hydrocarbon solvents of the soluble chromium compounds is not critical and can vary over wide limits, for example, such values can range from 0.1 g/liter of compound to the solubility limits of the chromium compound in the solvent in question, at a temperature of 20° C.

The amount of soluble acid phosphate added to the solution of chromium compound can also vary over wide limits, depending on the chromium compound in question and the phosphate used. In general, an amount of phosphate which introduces between 0.001 and 2.5 gram atoms of phosphorus per gram atom of chromium is suitable, although these limits can be exceeded without disadvantage. Preferably, it suffices to employ amounts of phosphate which introduce from 0.01 to 1 gram atom of phosphorus per gram atom of chromium.

To carry out the process of the invention, it suffices to simply add the acid phosphate or the mixture of acid phosphate partial esters to the solution of the chromium compound, the said solution being maintained at ambient temperature or being heated to a higher temperature in order to facilitate dissolution of the stabilizer. It is also possible to add the chromium compound to the organic solution of the stabilizer, or simultaneously to dissolve the chromium compound and the acid phosphate in the particular solvent.

In order to further illustrate the present invention and the advantages thereof, the following specific examples are given, it being understood that same are intended only as illustrative and in no wise limitative.

EXAMPLE 1

A solution of t-butyl chromate in cyclohexane was prepared by reacting 190 g of an aqueous solution of $CrO_3$, containing 30.2% of chromium metal, with 440 cm³ of t-butanol in 1,540 cm³ of cyclohexane, in the presence of 130 cm³ of water. The reaction was carried out at 20° C. The reaction mixture was stirred for 1 hour and the aqueous layer was then removed by decantation. A solution of t-butyl chromate in cyclohexane, containing 2.95% by weight of chromium metal, was thus obtained.

Upon maintaining this solution at ambient temperature, the appearance of a red-brown precipitate was observed after storage for 2 hours.

On the other hand, when 1 g of monooctyl orthophosphate was added to 150 g of the cyclohexane solution (ratio of the number of g. atoms of phosphorus to the number of g. atoms of Cr=0.056), no formation of precipitate was observed after storage for 240 hours.

EXAMPLE 2

1 g of monoisobutyl orthophosphate was added to 150 g of the cyclohexane solution of Example 1: ratio P/Cr=0.076. No deposit or precipitate was observed after storage for 240 hours.

EXAMPLE 3

A 10% strength solution of tert.-butyl chromate in cyclohexane was prepared in accordance with the procedure of Example 1.

150 g of the solution of tert.-butyl chromate in cyclohexane and 0.5 g of a phosphoric acid ester or of a mixture of phosphoric acid esters were introduced into a series of flat-bottomed tubes. After brief stirring, the tubes were maintained at 25° for 300 hours.

It was then determined that the control tube, without any stabilizer, contained 1.3 g of precipitate, whereas the amounts of precipitate were far less in the various tubes to which the stabilizers according to the invention had been added.

The experimental results are reported in the following table.

TABLE

| | Phosphoric acid stabilizer | | |
|---|---|---|---|
| | Orthophosphoric acid ester | Pyrophosphoric acid ester | % by weight orthophosphoric acid ester total phosphoric acid ester | Stabilization results (mass of precipitate after 300 hours) |
| Experiment No. 1 | isobutyl | isobutyl | 97 | 0.6 gram |
| Experiment No. 2 | isobutyl | isobutyl | 92 | 0.05 gram |
| Experiment No. 3 | isobutyl | isobutyl | 83 | 0 |
| Experiment No. 4 | isobutyl | isobutyl | 70 | 0.1 gram |
| Experiment No. 5 | 2-ethylhexyl | 2-ethylhexyl | 92 | 0.12 gram |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A composition of matter storage-stabilized against precipitation, comprising a hydrocarbon solvent solution of an organic compound of hexavalent chromium, and including a precipitation stabilizing amount of a partial ester of a phosphoric acid, said partial ester comprising at least one free acid group, O←P—OH, and at least one esterified acid group directly bonded to an acidic phosphorus atom, said esterified acid group being of the formula —OR wherein R is a saturated hydrocarbon radical containing from 1 to 18 carbon atoms, and said partial ester being soluble in said hydrocarbon solvent.

2. The composition of matter as defined by claim 1, said solvent solution comprising an orthophosphate stabilizer having the structural formula:

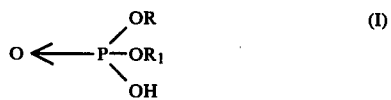

wherein R is a saturated hydrocarbon having from 1 to 18 carbon atoms, and $R_1$ is hydrogen or R.

3. The composition of matter as defined by claim 2, wherein either or both of the radicals R and $R_1$ contain at least 3 carbon atoms.

4. The composition of matter as defined by claim 1, said solvent solution comprising a pyrophosphate stabilizer having the structural formula:

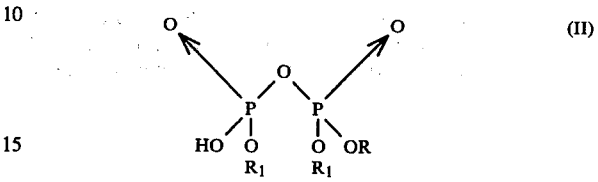

wherein R is a saturated hydrocarbon having from 1 to 18 carbon atoms, and $R_1$ is hydrogen or R.

5. The composition of matter as defined by claim 4, wherein either or both of the radicals R and $R_1$ contain at least 3 carbon atoms.

6. The composition of matter as defined by claim 1, said solvent solution comprising a stabilizing admixture of (i) an orthophosphate stabilizer having the structural formula:

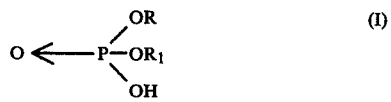

and (ii) a pyrophosphate stabilizer having the structural formula:

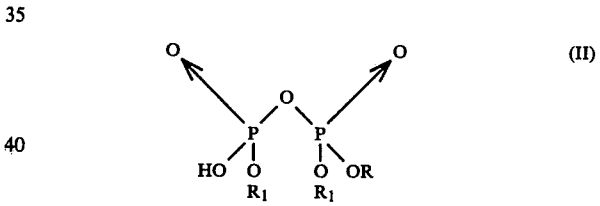

wherein the orthophosphate (I) comprises from 70 to 95% by weight of said admixture, and further wherein R is a saturated hydrocarbon having from 1 to 18 carbon atoms, and $R_1$ is hydrogen or R.

7. The composition of matter as defined by claim 1, 2, 3, 4, 5 or 6, said solvent comprising from 0.001 to 2.5 g. atoms of phosphorous per g. atom of chromium in solution.

8. The composition of matter as defined by claim 1, said hexavalent chromium compound being a chromate of an aliphatic or cycloaliphatic tertiary alcohol containing from 4 to 20 carbon atoms.

9. The composition of matter as defined by claim 7, said solvent solution comprising at least 0.1 g/liter of hexavalent chromium compound.

10. The composition of matter as defined by claim 1, said hydrocarbon solvent being selected from the group consisting of linear or branched chain alkanes containing from 5 to 9 carbon atoms, cycloalkanes containing from 5 to 9 carbon atoms, cycloalkanes containing from 5 to 9 carbon atoms and bearing from 1 to 3 alkyl substituents containing from 1 to 4 carbon atoms, and aromatic hydrocarbons.

11. The composition of matter as defined by claim 10, said hydrocarbon solvent being selected from the group consisting of n-pentane, n-hexane, 2-methylpentane, 3-methylpentane, 2,3-dimethylbutane, n-heptane, n-pentadecane, cyclopentane, cyclohexane, cycloheptane, cyclooctane, methylcyclohexane, benzene, toluene, xylene and ethylbenzene.

12. The composition of matter as defined by claim 8, said hydrocarbon solvent being a cycloalkane.

13. The composition of matter as defined by claim 12, said hydrocarbon solvent being cyclohexane.

14. The composition of matter as defined by claim 2, wherein R is selected from the group consisting of methyl, ethyl, isopropyl, butyl, t-butyl, heptyl, octyl, dodecyl, octadecyl, cyclohexyl, cyclooctyl, cyclododecyl, menthyl, phenyl, tolyl, benzyl and phenylethyl.

15. The composition of matter as defined by claim 4, wherein the pyrophosphate stabilizer is selected from the group consisting of dimethyl pyrophosphate, diethyl pyrophosphate, dibutyl pyrophosphate, diisobutyl pyrophosphate, dioctyl pyrophosphate, di-(2-ethylhexyl) pyrophosphate and butyl benzyl pyrophosphate.

16. The composition of matter as defined by claim 2, wherein R is a branched chain saturated hydrocarbon.

* * * * *